(12) United States Patent
Parthasaradhi Reddy et al.

(10) Patent No.: US 8,361,507 B2
(45) Date of Patent: Jan. 29, 2013

(54) EPROSARTAN MESYLATE CRYSTALLINE PARTICLES AND A PROCESS FOR PREPARING PURE EPROSARTAN

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Medabalimi Peter Paul Raj, Hyderabad (IN)

(73) Assignee: Hetero Drugs Limited (IN)

( * ) Notice: Subject to any disclaimer, the term of this patent is extended or adjusted under 35 U.S.C. 154(b) by 0 days.

(21) Appl. No.: 11/993,513

(22) PCT Filed: Jul. 25, 2007

(86) PCT No.: PCT/IN2007/000309
§ 371 (c)(1),
(2), (4) Date: Dec. 21, 2007

(87) PCT Pub. No.: WO2009/013760
PCT Pub. Date: Jan. 29, 2009

(65) Prior Publication Data
US 2010/0166850 A1    Jul. 1, 2010

(51) Int. Cl.
*A61K 9/14* (2006.01)
(52) U.S. Cl. .................................................. 424/489
(58) Field of Classification Search .................. None
See application file for complete search history.

(56) References Cited

U.S. PATENT DOCUMENTS

| 5,185,351 A | 2/1993 | Finkelstein |
| 6,262,102 B1 | 7/2001 | Duddu et al. |
| 2002/0071870 A1* | 6/2002 | Sharma .................. 424/489 |
| 2008/0220069 A1* | 9/2008 | Allison .................. 424/489 |

FOREIGN PATENT DOCUMENTS

| WO | 9736874 A1 | 10/1997 |
| WO | 0053282 A1 | 9/2000 |

OTHER PUBLICATIONS

PCT Noification of Transmittal of the International Search Report and the Written Opinion of the International Searching Authority or the Declaration, dated:Jul. 22, 2009.
PCT Written Opinion of the International Searching Authority, dated:Jul. 22, 2009.
International Patent Application No. PCT/IN06/000507, pp. 1-13, dated:Dec. 27, 2006.
International Search Report; International Application No. PCT/IN2006/000507; International Filing Date Dec. 27, 2006; 3 pages.
Written Opinion of the International Searching Authority; International Application No. PCT/IN2006/000507; International Filing Date Dec. 27, 2006; 3 pages.

* cited by examiner

*Primary Examiner* — Bethany Barham
(74) *Attorney, Agent, or Firm* — Cantor Colburn LLP

(57) ABSTRACT

The present invention relates to eprosartan mesylate particles having a relatively larger surface area, to the methods for the manufacture of said crystalline particles, and to pharmaceutical compositions comprising said crystalline particles. The present invention further relates to a crystalline solid of eprosartan acetate, to a process for its preparation and to a pharmaceutical composition comprising it. The present invention also provides substantially pure eprosartan free base and a process for its preparation.

18 Claims, 2 Drawing Sheets

EPROSARTAN MESYLATE CRYSTALLINE PARTICLES AND A PROCESS FOR PREPARING PURE EPROSARTAN

FIELD OF THE INVENTION

The present invention relates to eprosartan mesylate particles having a relatively large surface area, to the methods for the manufacture of said crystalline particles, and to pharmaceutical compositions comprising said crystalline particles. The present invention further relates to crystalline solid eprosartan acetate, to a process for its preparation and to a pharmaceutical composition comprising it. The present invention also provides substantially pure eprosartan free base and process for its preparation.

BACKGROUND OF THE INVENTION

U.S. Pat. No. 5,185,351 disclosed a variety of imidazolylalkenoic acid derivatives, processes for their preparation, pharmaceutical compositions in which they are present and uses thereof. These compounds are angiotensin II receptor antagonists and are useful in regulating hypertension induced or exacerbated by angiotensin II, and in the treatment of congestive heart failure, renal failure, and glaucoma. Among them, eprosartan mesylate, chemically (αE)-α-[[2-n-Butyl-1-[(4-carboxyphenyl)methyl]-1H-imidazol-5-yl]methylene-2-thiophenepropanoic acid monomethanesulfonate is a promising angiotensin II receptor antagonist useful in the treatment of hypertension, congestive heart failure and renal failure. Eprosartan is represented by the following structure:

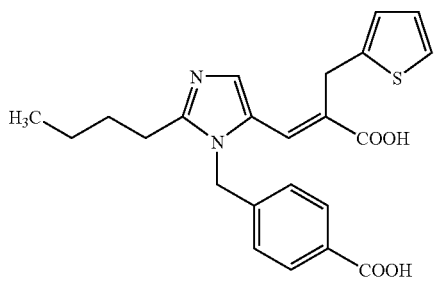 [SMILES: CCCCc1ncc(/C=C(\Cc2cccs2)C(=O)O)n1Cc1ccc(C(=O)O)cc1]

As per the process described and exemplified in the U.S. Pat. No. 5,185,351 (herein after referred to as the '351 patent), eprosartan free base (obtained as per the processes described in example I of the '351 patent) is suspended in isopropyl alcohol under stirring at about 8° C., methanesulfonic acid is added rapidly to the stirred suspension, the mass cooled to 3° C. and the precipitated solid collected to give crude eprosartan mesylate. The crude eprosartan mesylate is further purified by dissolving crude eprosartan mesylate in acetic acid at 80° C., filtered through a hyflow bed at 80° C., the solution cooled slowly to 25° C. followed by stirring and then the precipitated solid is collected by adding ethyl acetate as an anti-solvent to give eprosartan mesylate.

PCT Patent Publication No. WO 97/36874 described processes for the preparation of eprosartan mesylate dihydrate. According to this publication, eprosartan mesylate dihydrate can be prepared either by i) recrystallizing the anhydrous form of eprosartan mesylate (obtained as per the process described in the '351 patent) from an aqueous solution containing an acid; or ii) mixing the anhydrous form of eprosartan mesylate with one or more pharmaceutically acceptable excipients, granulating the mixture with water, and drying the granulation to a predetermined water content.

According to U.S. Pat. No. 6,262,102 B1, monohydrated form of eprosartan mesylate is produced during the vacuum drying of the dihydrated form of this compound or when the anhydrate of eprosartan mesylate is granulated with water, stored at 50° C. overnight and vacuum dried overnight at ambient temperature.

PCT Patent Application No. PCT/IN06/000507 described an improved process for the preparation of eprosartan and its pharmaceutically acceptable acid addition salts thereof in high purity which comprises: a) reacting methyl 4-[[2-butyl-5-formyl-1H-imidazol-1-yl]methyl]benzoate with ethyl 2-carboxy-3-(2-thienyl)propionate in the presence of a base in a solvent selected from cyclohexane and n-hexane to afford a diester intermediate, namely ethyl (αE)-α-[[2-n-butyl-1-[[4-(methoxycarbonyl)phenyl]methyl]-1H-imidazol-5-yl]methylene-2-thiophene propionate, substantially free of a decarboxylate impurity namely, ethyl 3-(2-thienyl)propionate; and b) hydrolyzing the diester intermediate with a base such as sodium or potassium hydroxide to obtain pure eprosartan.

The processes described in the prior art produce eprosartan mesylate particles having the specific surface area at below 0.6 m$^2$/g as measured by Brunauer-Emmett-Teller method (B.E.T), and the mean particle size ($D_{50}$) of about 65 μm to about 75 μm and 90 volume-% of the particles ($D_{90}$) of about 200 μm to about 215 μm, resulting in similarly poor dissolution and solubility properties.

Specific surface area of an active pharmaceutical ingredient may be affected by various factors. There is a general connection between Specific Surface Area and Particle Size Distribution; the smaller the Particle Size Distribution, the higher the Specific Surface Area. The rate of dissolution of a poorly-soluble drug is a rate-limiting factor in its absorption by the body. A reduction in the particle size can increase the dissolution rate of such compounds through an increase in the surface area of the solid phase that is in contact with the liquid medium, thereby resulting in an enhanced bioavailability of the compositions containing such compounds. It is generally not possible to predict the exact particle size and distribution required for any particular drug substance to achieve a specific dissolution profile or a specific in vivo behavior, as different drugs show differing dissolution characteristics with a reduction in the particle size.

Eprosartan mesylate is a white to off-white crystalline substance, soluble in methanol, but practically insoluble in water. The lack of solubility of eprosartan mesylate creates a problem since bioavailability of a water insoluble active ingredient is usually poor. Thus there is a need in the art to prepare active pharmaceutical ingredients such as eprosartan mesylate particles with a desired surface area to obtain formulations with greater bioavailability, and to compensate for any loss of surface area before formulation.

PCT Patent Publication No. WO 00/53282 disclosed eprosartan mesylate crystalline particles with a $d_{90}$ value of less than 10 micron, a process for the preparation of said particles which comprises contacting a stream of eprosartan mesylate dissolved in a solvent, preferably acetic acid, with a stream of anti-solvent, preferably tert-butyl methyl ether, or colder solvent, or a solution of an appropriate acid or base, and separating off the crystals formed.

It is well recognized that preparation of tablets with a reproducible composition requires that all the dry ingredients have good flow properties. In cases where the active ingredient has good flow properties, tablets can be prepared by direct compression of the ingredients. However, in many cases the particle size of the active substance is very small, the active substance is cohesive or has poor flow properties.

The eprosartan mesylate product prepared by methods as outlined in the PCT Patent Publication No. WO 00/53282 has a very small particle size i.e., crystalline particles with a $d_{90}$ value less than 10 micron resulting in similarly poor flow properties.

Thus, there is a need in the art for eprosartan mesylate with a desirable particle size distribution, which has good flow properties, and better dissolution and solubility properties.

Extensive laboratory and full-scale research has resulted in a new and inventive crystallization process producing eprosartan mesylate crystalline particles having a specific surface area of from about 0.65 $m^2/g$ to about 3 $m^2/g$. Said particles are useful for the manufacture of directly compressed tablets. Accurate dosing in capsules may also be achieved with such particles.

Even though the U.S. Pat. No. 5,185,351 mentioned pharmaceutically acceptable salts of eprosartan, the acetate salt of eprosartan is not isolated as a solid and characterized. It has been found that the acetate salt of eprosartan can be isolated in a pure form from the crude eprosartan free base. It has also been found that the solid form of eprosartan acetate is a useful intermediate in the preparation of eprosartan free base or a pharmaceutically acceptable salt thereof in high purity.

According to one object, the present invention provides eprosartan mesylate and formulations containing eprosartan mesylate particles having a specific surface area of from about 0.65 $m^2/g$ to about 3 $m^2/g$.

According to another object, the present invention provides eprosartan mesylate and formulations containing eprosartan mesylate particles having mean particle size ($D_{50}$) ranges from about 7 μm to 60 μm and 90 volume-% of the particles ($D_{90}$) ranges from about 21 μm to 150 μm.

Another object of the present invention is to provide a crystalline solid of eprosartan acetate, process for preparing it and a pharmaceutical composition comprising it.

Another object of the present invention is to provide substantially pure eprosartan free base and process for its preparation.

DETAILED DESCRIPTION OF THE INVENTION

According to one aspect of the present invention, there is provided crystalline particles of eprosartan mesylate having a specific surface area of from about 0.65 $m^2/g$ to about 3 $m^2/g$.

According to another aspect of the present invention, there is provided crystalline particles of eprosartan mesylate having mean particle size ($D_{50}$) ranges from about 7 μm to 50 μm and 90 volume-% of the particles ($D_{90}$) ranges from about 21 μm to 150 μm.

According to another aspect of the present invention, a process is provided for the preparation of eprosartan mesylate crystalline particles having a specific surface area of from about 0.65 $m^2/g$ to about 3 $m^2/g$, which comprises:
a) suspending eprosartan free base or its acetate salt in a ketonic solvent;
b) adding methanesulfonic acid slowly to the suspension obtained in step (a) at a temperature below 10° C.; and
c) collecting the precipitated eprosartan mesylate crystalline particles having a specific surface area of from about 0.65 $m^2/g$ to about 3 $m^2/g$.

A preferable ketonic solvent is selected from the group consisting of acetone, methyl ethyl ketone, methyl isobutyl ketone, methyl isopropyl ketone, methyl tert-butyl ketone and the more preferable ketonic solvent is acetone.

The solution formed after addition of methanesulfonic acid in step (b) is preferably stirred at least for about 1 hour at 20-30° C., more preferably stirred at least for about 1 hour 30 minutes at 20-30° C. and still more preferably stirred for about 2 hours to 6 hours at 20-30° C.

The precipitated eprosartan mesylate crystalline particles in step (c) are collected by filtration or centrifugation.

Preferably eprosartan mesylate particles obtained by the process described above have a specific surface area of from about 0.7 to 2.5 $m^2/g$, and more preferably of from about 0.8 to 2.0 $m^2/g$.

Preferably eprosartan mesylate particles obtained by the processes described above have mean particle size ($D_{50}$) ranges from about 10 μm to 30 μm and 90 volume-% of the particles ($D_{90}$) ranges from about 22 μm to 120 μm; more preferably have mean particle size ($D_{50}$) ranges from about 10 μm to 25 μm and 90 volume-% of the particles ($D_{90}$) ranges from about 25 μm to 60 μm; and still more preferably have mean particle size ($D_{50}$) ranges from about 11 μm to 20 μm and 90 volume-% of the particles ($D_{90}$) ranges from about 26 μm to 50 μm.

As used herein, the term "μm" refers to "micrometer" which is $1\times10^{-6}$ meter.

As used herein, "crystalline particles" means any combination of single crystals, aggregates and agglomerates.

As used herein "Particle Size Distribution (P.S.D.)" means the cumulative volume size distribution of equivalent spherical diameters as determined by laser diffraction at 1 bar dispersive pressure in a Sympatec Helos equipment. "Mean particle size distribution, i.e., d(0.5)" correspondingly, means the median of said particle size distribution.

Specific surface area is defined in units of square meters per gram ($m^2/g$). It is usually measured by nitrogen absorption analysis. In this analysis, nitrogen is absorbed on the surface of the substance. The amount of the absorbed nitrogen (as measured during the absorption or the subsequent desorption process) is related to the surface area via a formula known as the B.E.T. formula.

According to another aspect of the present invention, there is provided a crystalline solid of eprosartan acetate.

According to another aspect of the present invention, the crystalline solid of eprosartan acetate is characterized by an X-ray powder diffraction pattern having peaks expressed as 2θ angle positions at about 8.1, 10.7, 14.5, 16.7, 17.8, 21.4, 22.5, 23.6, 24.6, 26.1 and 28.4±0.2 degrees. The typical X-ray powder diffraction pattern is shown in FIG. 1.

According to another aspect of the present invention, the crystalline solid of eprosartan acetate is further characterized by a Differential Scanning calorimetry (DSC) thermogram having a small endotherm 110° C. followed by a sharp endotherm at 266° C. The typical DSC thermogram is shown in FIG. 2.

According to another aspect of the present invention, a process is provided for the preparation of crystalline solid eprosartan acetate, which comprises:
a) dissolving crude eprosartan free base in acetic acid;
b) adding methylene chloride slowly to the solution obtained in step (a) at a temperature below about 40° C.; and
c) collecting the precipitated eprosartan acetate crystalline solid.

The purity (measured by HPLC) of the eprosartan acetate obtained according to the present invention is preferably about above 99%, more preferably about above 99.5% and still more preferably about above 99.9%.

Crude eprosartan free base used as starting material may be used in the form of a residue or a crystalline form, obtained by processes described in the art.

The term 'crude eprosartan free base' in the specification refers to eprosartan free base having HPLC purity below 98.5%.

Preferably the crude eprosartan free base in step (a) may be dissolved in acetic acid at a temperature above about 40° C., more preferably at a temperature between 45° C. and 110° C. and still more preferably at a temperature between 50° C. and 100° C.

The solution obtained in step (a) may optionally be subjected to carbon treatment and then used in the next step.

Preferably methylene chloride may be added to the filtrate in step (b) at a temperature between 0° C. and 40° C., more preferably at a temperature between 10° C. and 40° C. and still more preferably at a temperature between 15° C. and 35° C.

The precipitated eprosartan acetate crystalline solid in step (c) is collected by filtration or centrifugation.

According to another aspect of the present invention, there is provided a substantially pure eprosartan free base.

According to another aspect of the present invention, there is provided a process for the preparation of substantially pure eprosartan free base, which comprises:
a) suspending eprosartan acetate in water;
b) adjusting the pH of the suspension to about 6.7-7.5 with a base; and
c) collecting the precipitated substantially pure eprosartan base.

The term "substantially pure eprosartan free base" in the specification refers to eprosartan free base having a purity (measured by HPLC) above 99.5%, preferably above about 99.7%, and more preferably above about 99.9%.

Preferably the pH of the suspension in the step (b) is adjusted to 6.8-7.4 and more preferably to 6.9-7.3.

The base used in step (b) is an organic base or an inorganic base. A preferable organic base is tributylamine, N,N-dimethylaniline, 4-dimethylaminopyridine, ethyldiisopropylamine, N-ethylmorpholine, 2,4,6-trimethylpyridine or triethylamine. A preferable inorganic base is an alkali or alkaline earth metal carbonate or bicarbonate or hydroxide, a more preferable inorganic base is sodium hydroxide or potassium hydroxide, and still a more preferable base is sodium hydroxide.

Preferably an aqueous solution of sodium hydroxide may be used to adjust the pH and more preferably dilute aqueous sodium hydroxide may be used.

The precipitated eprosartan free base in step (c) is collected by filtration or centrifugation.

According to another aspect of the present invention there is provided a pharmaceutical composition comprising eprosartan mesylate crystalline particles having a specific surface area of from about 0.65 $m^2/g$ to about 3 $m^2/g$ and one or more pharmaceutically inert excipients.

A preferable pharmaceutical composition of eprosartan mesylate crystalline particles has a specific surface area of from about 0.65 $m^2/g$ to about 3 $m^2/g$ is selected from a solid dosage form and an oral suspension.

According to another aspect of the present invention there is provided a pharmaceutical composition comprising eprosartan mesylate crystalline particles having mean particle size ($D_{50}$) ranges from about 7 µm to 50 µm and 90 volume-% of the particles ($D_{90}$) ranges from about 21 µm to 150 µm and one or more pharmaceutically inert excipients.

A preferable pharmaceutical composition of eprosartan mesylate crystalline particles has mean particle size ($D_{50}$) ranges from about 7 µm to 50 µm and 90 volume-% of particles ($D_{90}$) ranges from about 21 µm to 150 µm is selected from a solid dosage form and a oral suspension.

The term "solid dosage form" as used herein includes conventional solid dosage forms such as tablet, capsule, granules, sachet, and the like.

Pharmaceutically inert excipients include all physiologically inert excipients used in the pharmaceutical art of dispensing. Examples include binders, diluents, surfactants, disintegrants, lubricants/glidants, coloring agents, and the like.

Specific examples of binders include methyl cellulose, hydroxypropyl cellulose, hydroxypropyl methylcellulose, polyvinylpyrrolidone, gelatin, gum Arabic, ethyl cellulose, polyvinyl alcohol, pullulan, pregelatinized starch, agar, tragacanth, sodium alginate, propylene glycol, and the like.

Specific examples of diluents include calcium carbonate, calcium phosphate-dibasic, calcium phosphate-tribasic, calcium sulfate, microcrystalline cellulose, cellulose powdered, dextrates, dextrins, dextrose excipients, fructose, kaolin, lactitol, lactose, mannitol, sorbitol, starch, starch pregelatinized, sucrose, sugar compressible, sugar confectioners, and the like and mixtures thereof.

Surfactants include both non-ionic and ionic (cationic, anionic and zwitterionic) surfactants suitable for use in pharmaceutical dosage forms. These include polyethoxylated fatty acids and its derivatives, for example, polyethylene glycol 400 distearate, polyethylene glycol-20 dioleate, polyethylene glycol 4-150 mono dilaurate, and polyethylene glycol-20 glyceryl stearate; alcohol-oil transesterification products, for example, polyethylene glycol-6 corn oil; polyglycerized fatty acids, for example, polyglyceryl-6 pentaoleate; propylene glycol fatty acid esters, for example, propylene glycol monocaprylate; mono and diglycerides, for example, glyceryl ricinoleate; sterol and sterol derivatives; sorbitan fatty acid esters and its derivatives, for example, polyethylene glycol-20 sorbitan monooleate and sorbitan monolaurate; polyethylene glycol alkyl ether or phenols, for example, polyethylene glycol-20 cetyl ether and polyethylene glycol-10-100 nonyl phenol; sugar esters, for example, sucrose monopalmitate; polyoxyethylene-polyoxypropylene block copolymers known as "poloxamer"; ionic surfactants, for example, sodium caproate, sodium glycocholate, soy lecithin, sodium stearyl fumarate, propylene glycol alginate, octyl sulfosuccinate disodium, and palmitoyl carnitine; and the like and mixtures thereof.

Specific examples of disintegrants include low-substituted hydroxypropylcellulose (L-HPC), sodium starch glycollate, carboxymethyl cellulose, calcium carboxymethyl cellulose, sodium carboxymethyl cellulose, croscarmellose sodium A-type (Ac-di-sol), starch, crystalline cellulose, hydroxypropyl starch, pregelatinized starch, and the like and mixtures thereof.

Specific examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like and mixtures thereof.

Coloring agents include any FDA approved colors for oral use.

Figure 1:
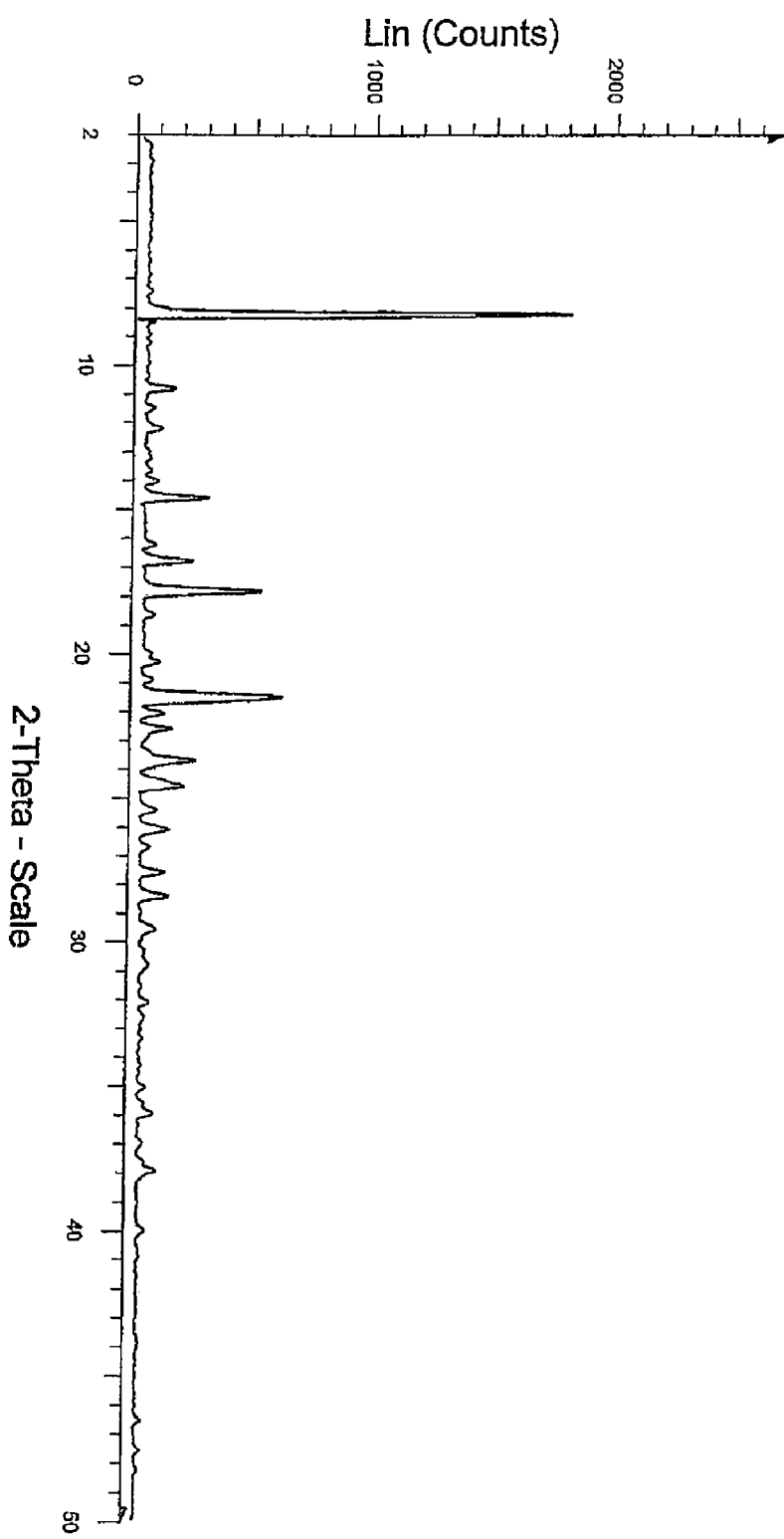
FIG. 1 shows a typical x-ray powder diffraction spectrum of crystalline solid pure eprosartan acetate.
Figure 2:
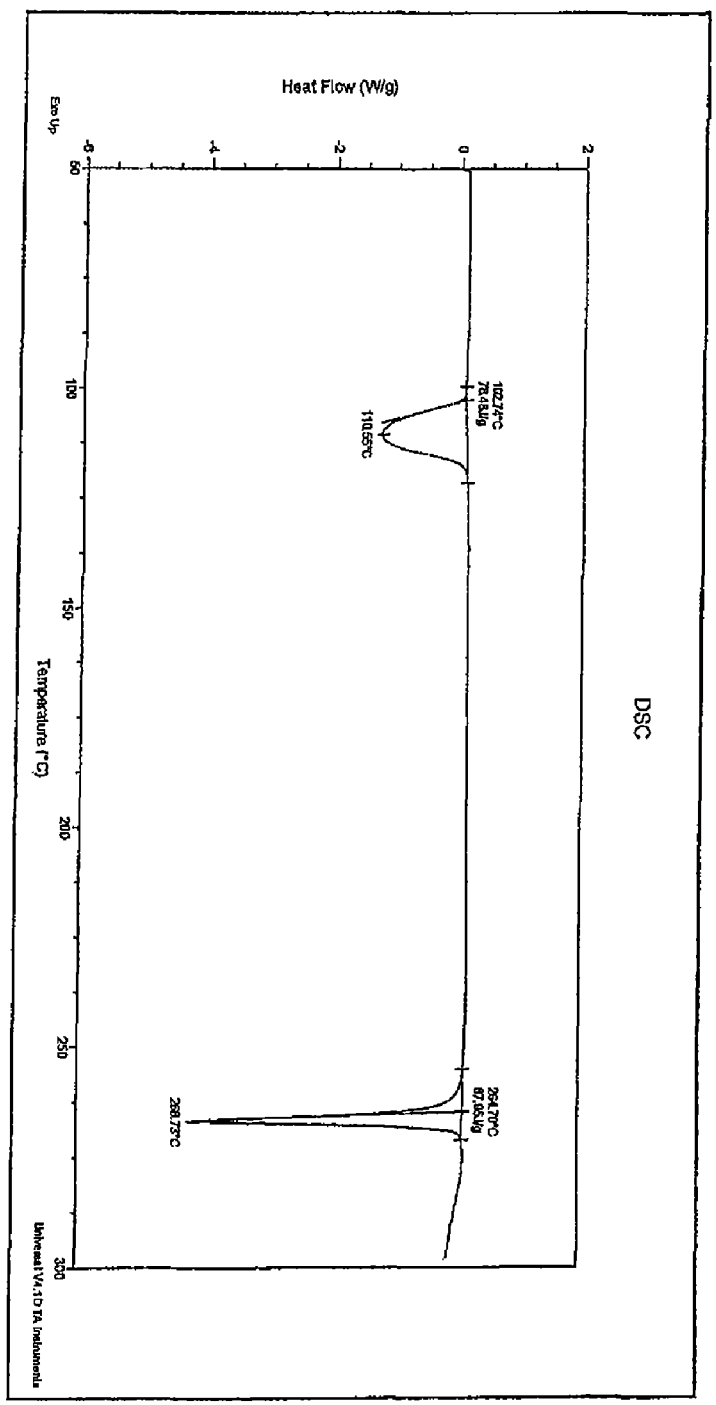
FIG. 2 shows a Differential Scanning calorimetry (DSC) thermogram of crystalline solid pure eprosartan acetate.

X-ray powder diffraction spectrum was measured on a bruker axs D8 advance X-ray powder diffractometer having a copper-$k_\alpha$ radiation. Approximately 1 gm of sample was gently flattened on a sample holder and scanned from 2 to 50 degrees two-theta, at 0.03 degrees two-theta per step and a step time of 0.5 seconds. The sample was simply placed on the sample holder. The sample was rotated at 30 rpm at a voltage 40 KV and 35 mA.

DSC (Differential Scanning calorimetry) measurements were performed with a DSC Q10 (TA Instruments, Inc.). About 3 mg of the powder was placed in an open aluminum pan and it is crimped with an aluminum lid. The crimped sample is then placed in the DSC cell opposite to empty aluminum pan (as reference) and the sample was scanned at 10° C./min from 50° C. to 300° C.

The following examples are given for the purpose of illustrating the present invention and should not be considered as limitation on the scope or spirit of the invention.

REFERENCE EXAMPLES

Reference Example 1

Methyl 4-[[2-butyl-5-formyl-1H-imidazol-1-yl]methyl] benzoate (32 gm) and ethyl 2-carboxy-3-(2-thienyl)propionate (57.15 gm) are added to cyclohexane (292 ml) under stirring at 25-30° C., the contents are heated to reflux (80-85° C.) for 2 hours under dean stark to separate the traces of water. The reaction mass is cooled to 50° C. and then slowly added a freshly prepared catalyst solution of propanoic acid (22.93 ml) in cyclohexane (53 ml) and piperidine (10.66 ml). The resulting mass is heated to reflux (80-85° C.) for 20 hours, and to the reaction mass drop wise was added a 50% NaOH solution (64 gm of NaOH in 256 ml of water) after reflux at 50° C. and then the reaction mass is heated to reflux for 2 hours. The reaction mass is cooled to 60° C., the layers separated, to the aqueous layer was added ethanol (192 ml) and then the pH of the mass is adjusted to 5.0 to 5.1 at 60° C. with 6N HCl solution (66 ml of HCl and 66 ml of water). The resulting mass was cooled to 20-25° C. and stirred for 2 hours. The mass was filtered, washed with water (100 ml) and then dried at 70-75° C. to give 26 gm of crude eprosartan free base (HPLC purity: 98.2%).

Reference Example 2

Crude eprosartan free base (50 gm, obtained in reference example 1) is stirred with isopropyl alcohol (750 ml), the reaction mass is cooled to 8° C. and then methane sulfonic acid (34 gm) is added drop wise to the mass at 0-5° C. The reaction mass is stirred for 5 hours 30 minutes at 0-5° C., the mass filtered, the material washed with isopropyl alcohol (138 ml) and then dried under vacuum at 45° C. to give 45.6 gm of crude eprosartan mesylate (HPLC purity: 98.7%).

Reference Example 3

Crude eprosartan mesylate (45.6 gm, obtained in reference example 2) is added to acetic acid (137 ml) under stirring at 25-30° C., the contents are heated to 80° C. to form a clear solution, filtered through a hyflow bed at 80° C. and the bed washed with hot acetic acid (45.6 ml). The filtrate is slowly cooled to 25° C., stirred for 2 hours 30 minutes, ethyl acetate (228 ml) is slowly added to the mass and then stirred for 1 hour. To the resulting mass again ethyl acetate (228 ml) is added and stirred for 18 hours for complete precipitation. The material is filtered, sucked dry, washed with ethyl acetate (108 ml) and then dried under vacuum at 40° C. to give 40.8 gm of eprosartan mesylate [HPLC purity: 99.1%; Specific Surface Area: 0.53 m$^2$/g; Mean particle size ($D_{50}$): 70.56 μm and 90 volume-% of the particles ($D_{90}$): 213.72 μm].

EXAMPLES

Example 1

Crude eprosartan free base (50 gm, HPLC purity: 98.2%) is added to acetic acid (200 ml) under stirring at 25-30° C., the contents are heated to 80° C., to the resulting mass is added activated carbon (5 gm) and then stirred for 1 hour. The mass is filtered through a hyflow bed and the bed washed with hot acetic acid (50 ml). The filtrate is cooled to 25-30° C., methylene chloride (750 ml) is added drop wise to the mass and then stirred for 24 hours at 25-30° C. The mass is cooled to 0-5° C. and then stirred for 2 hours. The material is filtered, washed with methylene chloride (43 ml) and then dried to give 30 gm of pure eprosartan acetate (HPLC purity: 99.82%).

Example 2

Eprosartan acetate (30 gm, obtained in example 1) is suspended in acetone (450 ml) at 25-30° C., the suspension is cooled to 0-5° C., methanesulfonic acid (21.2 gm) is added drop wise while maintaining the temperature at 0-5° C. The temperature of the mass is raised to 25-30° C. and stirred for 5 hours. The mass is cooled to 0-5° C., stirred for 1 hour, the material is filtered and then suck dried. To the resulting wet cake is added acetone (60 ml) and stirred for 30 minutes at 25-30° C. The material is filtered, washed with acetone (30 ml) and then dried to give 29 gm of pure eprosartan mesylate [HPLC Purity: 99.95%; Specific Surface Area: 1.09 m$^2$/g; Mean particle size ($D_{50}$): 12.13 μm and 90 volume-% of the particles ($D_{90}$): 33.48 μm].

Example 3

Eprosartan acetate (10 gm, obtained in example 1) is suspended in water (50 ml) at 25-30° C. and the pH of the suspension is adjusted to 7.0-7.25 with 5% sodium hydroxide solution (23 ml). The material is filtered, washed with water (20 ml) and then dried to give 8 gm of pure eprosartan free base (HPLC Purity: 99.85%).

Example 4

Eprosartan free base (8 gm, obtained in example 3) is suspended in acetone (120 ml) at 25-30° C., the suspension is cooled to 0-5° C., methanesulfonic acid (5.4 gm) is added drop wise while maintaining the temperature at 0-5° C. The temperature of the mass is raised to 25-30° C. and stirred for 5 hours. The mass is cooled to 0-5° C., stirred for 1 hour, the material is filtered and then suck dried. To the resulting wet cake is added acetone (16 ml) and stirred for 15 minutes at 25-30° C. The material is filtered, washed with acetone (8 ml) and then dried to give 9 gm of pure eprosartan mesylate [HPLC Purity: 99.96%; Specific Surface Area: 1.11 m$^2$/g; Mean particle size ($D_{50}$): 11.23 μm and 90 volume-% of the particles ($D_{90}$): 30.42 μm].

Without further elaboration of the foregoing will so fully illustrate our invention that others may, by applying current or future knowledge, adapt the same for use under various conditions of service.

We claim:

1. Crystalline particles of eprosartan mesylate having a specific surface area of from about 0.65 m$^2$/g to about 3 m$^2$/g prepared by the process comprising
   a) suspending eprosartan free base or its acetate salt in a ketonic solvent;
   b) adding methanesulfonic acid slowly to the suspension obtained in step (a) at a temperature below 10° C.; and
   c) collecting the precipitated eprosartan mesylate crystalline particles having a specific surface area of from about 0.65 m$^2$/g to about 3 m$^2$/g.

2. The crystalline particles of eprosartan mesylate as claimed in claim 1, wherein the particles have mean particle size ($D_{50}$) ranges from about 7 μm to 50 μm and 90 volume-% of the particles ($D_{90}$) ranges from about 21 μm to 150 μm.

3. A process for the preparation of eprosartan mesylate crystalline particles having a specific surface area of from about 0.65 m$^2$/g to about 3 m$^2$/g as defined in claim 1, which comprises:
   a) suspending eprosartan free base or its acetate salt in a ketonic solvent;
   b) adding methanesulfonic acid slowly to the suspension obtained in step (a) at a temperature below 10° C.; and
   c) collecting the precipitated eprosartan mesylate crystalline particles having a specific surface area of from about 0.65 m$^2$/g to about 3 m$^2$/g.

4. The process as claimed in claim 3, wherein the ketonic solvent is selected from the group consisting of acetone, methyl ethyl ketone, methyl isobutyl ketone, methyl isopropyl ketone, methyl tert-butyl ketone.

5. The process as claimed in claim 4, wherein the ketonic solvent is acetone.

6. The process as claimed in claim 3, wherein the solution formed after addition of methanesulfonic acid in step (b) is stirred at least for about 1 hour at 20-30° C.

7. The process as claimed in claim 6, wherein the solution is stirred at least for about 1 hour 30 minutes at 20-30° C.

8. The process as claimed in claim 7, wherein the solution is stirred for about 2 hours to 6 hours at 20-30° C.

9. The process as claimed in claim 3, wherein the precipitated eprosartan mesylate crystalline particles in step (c) are collected by filtration or centrifugation.

10. The process as claimed in claim 3, wherein the eprosartan mesylate particles obtained in step (c) have a specific surface area of from about 0.7 to 2.5 m$^2$/g.

11. The process as claimed in claim 10, wherein the eprosartan mesylate particles have a specific surface area of from about 0.8 to 2.0 m$^2$/g.

12. The process as claimed in claim 3, wherein the eprosartan mesylate particles obtained in step (c) have mean particle size ($D_{50}$) ranges from about 10 μm to 30 μm and 90 volume-% of the particles ($D_{90}$) ranges from about 22 μm to 120 μm.

13. The process as claimed in claim 12, wherein eprosartan mesylate particles have mean particle size ($D_{50}$) ranges from about 10 μm to 25 μm and 90 volume-% of the particles ($D_{90}$) ranges from about 25 μm to 60 μm.

14. The process as claimed in claim 13, wherein eprosartan mesylate particles have mean particle size ($D_{50}$) ranges from about 11 μm to 20 μm and 90 volume-% of the particles ($D_{90}$) ranges from about 26 μm to 50 μm.

15. A pharmaceutical composition comprising eprosartan mesylate crystalline particles having a specific surface area of from about 0.65 m$^2$/g to about 3 m$^2$/g and one or more pharmaceutically inert excipients; the eprosartan mesylate crystalline particles prepared by the process comprising
   a) suspending eprosartan free base or its acetate salt in a ketonic solvent;
   b) adding methanesulfonic acid slowly to the suspension obtained in step (a) at a temperature below 10° C.; and
   c) collecting the precipitated eprosartan mesylate crystalline particles having a specific surface area of from about 0.65 m$^2$/g to about 3 m$^2$/g.

16. The pharmaceutical composition as claimed in claim 15, wherein the eprosartan mesylate crystalline particles having mean particle size ($D_{50}$) ranges from about 7 μm to 50 μm and 90 volume-% of the particles ($D_{90}$) ranges from about 21 μm to 150 μm.

17. The pharmaceutical composition as claimed in claim 15, wherein the pharmaceutical composition is selected from a solid dosage form and an oral suspension.

18. The pharmaceutical composition as claimed in claim 17, wherein solid dosage form includes tablet, capsule, granules and sachet.

* * * * *